US009775919B2

(12) United States Patent
Pattayil et al.

(10) Patent No.: US 9,775,919 B2
(45) Date of Patent: Oct. 3, 2017

(54) CURCUMIN COATED MAGNETITE NANOPARTICLES FOR BIOMEDICAL APPLICATIONS

(71) Applicant: COUNCIL OF SCIENTIFIC & INDUSTRIAL RESEARCH, New Delhi (IN)

(72) Inventors: Alias Joy Pattayil, Maharashtra (IN); Kunnoth Naduvilidam Jayaprabha, Pune (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 15/202,716

(22) Filed: Jul. 6, 2016

(65) Prior Publication Data
US 2016/0310620 A1 Oct. 27, 2016

Related U.S. Application Data

(63) Continuation of application No. 14/372,698, filed as application No. PCT/IN2013/000030 on Jan. 17, 2013.

(30) Foreign Application Priority Data

Jan. 17, 2012 (IN) .............................. 138/DEL/2012

(51) Int. Cl.
*A61K 9/00* (2006.01)
*A61K 49/18* (2006.01)
*A61K 9/51* (2006.01)
*A61K 31/12* (2006.01)
*A61K 9/16* (2006.01)
*A61K 49/00* (2006.01)
*A61K 49/10* (2006.01)
*A61K 9/50* (2006.01)
*B82Y 5/00* (2011.01)
*B82Y 15/00* (2011.01)

(52) U.S. Cl.
CPC ........ *A61K 49/1833* (2013.01); *A61K 9/0009* (2013.01); *A61K 9/1676* (2013.01); *A61K 9/1682* (2013.01); *A61K 9/5094* (2013.01); *A61K 9/51* (2013.01); *A61K 9/5123* (2013.01); *A61K 31/12* (2013.01); *A61K 49/0052* (2013.01); *A61K 49/10* (2013.01); *B82Y 5/00* (2013.01); *B82Y 15/00* (2013.01)

(58) Field of Classification Search
CPC ....... A61K 9/00; A61K 49/00; A61K 49/1833
See application file for complete search history.

(56) References Cited

U.S. PATENT DOCUMENTS

2013/0171215 A1* 7/2013 Sahoo .................. A61K 9/0014
424/400

OTHER PUBLICATIONS

International Search Report and Written Opinion of the International Searching Authority, PCT Application No. PCT/IN2013/000030, Council of Scientific & Industrial Research, dated Apr. 12, 2013.
International Preliminary Report on Patentability, PCT/IN2013/000030, Council of Scientific & Industrial Research, dated May 23, 2014.
F. Dilnawaz, et al., "Transferrin-conjugated curcumin-loaded superparamagnetic iron oxide nanoparticles induce augmented cellular uptake and apoptosis in K562 cells," Acta Biomaterialia 8 (2012) 704-719.
Murali M. Yallapu, et al., "Curcumin-loaded magnetic nanoparticles for breast cancer therapeeutics and imaging applications," International Journal of Nanomedicine, 2012:7 1761-1779.
Lam Dai Tran, et al., "Nanosized magnetofluorescent Fe304-curcumin conjugate for multimodal monitoring and drug targeting," Colloids and Surfaces A: Physiochem. Eng. Aspects 371 (2010), 104-112.
S.F. Medeiros, et al., "Stimuli-responsive magnetic particles for biomedical applications," International Journal of Pharmaceutics 403 (2011) 139-161.
P. Bowen, "Particle Size Distribution Measurement from Millimeters to Nanometers and Rods to Platelets," Journal of Dispersion Science and Technology, vol. 23, No. 5, pp. 631-662, Jan. 1, 2002.

* cited by examiner

*Primary Examiner* — Michael G Hartley
*Assistant Examiner* — Jagadishwar Samala
(74) *Attorney, Agent, or Firm* — McDonald Hopkins LLC (57) ABSTRACT

The present invention discloses biocompatible, stable curcumin or its derivatives coated ultra-small super paramagnetic iron oxide nanoparticles (USPION) for biomedical applications. Disclosed herein is also a simple one-pot process for the synthesis of biocompatible, stable curcumin or its derivatives coated ultra-small superparamagnetic iron oxide nanoparticles in absence of a linker or binder. The curcumin or its derivatives coated ultra-small super paramagnetic iron oxide nanoparticles of the present invention retains the medicinal, radical scavenging and fluorescence properties of curcumin.

5 Claims, 6 Drawing Sheets

CURCUMIN COATED MAGNETITE NANOPARTICLES FOR BIOMEDICAL APPLICATIONS

CROSS REFERENCE TO RELATED APPLICATIONS

This application is a Continuation of U.S. application Ser. No. 14/372,698 entitled "Curcumin Coated Magnetite Nanoparticles for Biomedical Applications" filed on Jul. 16, 2014 which is a 35 U.S.C. 371 national stage filing of PCT Application No. PCT/IN2013/000030, entitled "Curcumin Coated Magnetite Nanoparticles for Biomedical Applications" filed on Jan. 17, 2013, which claims the benefit of Indian Application No. 138/DEL/2012 filed on Jan. 17, 2012, each of which is incorporated herein in its entirety by reference.

TECHNICAL FIELD OF INVENTION

Present invention relates to curcumin coated magnetite nanoparticles, which are biocompatible, stable curcumin or its derivatives coated ultra-small superparamagnetic iron oxide nanoparticles (USPION) for biomedical applications. The invention further relates to a simple one-pot process for the synthesis of biocompatible, stable curcumin or its derivatives coated ultra-small superparamagnetic iron oxide nanoparticles in absence of a linker or binder. The curcumin or its derivatives coated ultra-small super paramagnetic iron oxide nanoparticles of the present invention retains the medicinal, radical scavenging and fluorescence properties of curcumin.

BACKGROUND OF THE INVENTION

Metal oxide nanoparticles are one of the most significant contributors towards the revolutionary change of nanostructured science and technology. Out of many metal oxides, multifunctional iron oxides have paved the way towards applications such as ferrofluids, colour imaging, recording media and magnetic refrigeration. Thrust areas of applications of iron oxides in biological field include contrast agents in MRI, in hyperthermia treatment and drug delivery. The prerequisite for all these applications are smaller size, superparamagnetism, biodegradability, monodispersed, water dispersible particles which have higher stability at room temperature (±20 degrees) and at physiological pH. The smaller size allows nanoparticles to cross through the cellular membranes and avoid the detection by the reticuloendothelial system as well as allow longer blood residence time and subject to rapid renal elimination.

Uncoated magnetite nanoparticles do not form stable dispersions in water at physiological pH. Apart from high surface energy (which is due to high surface area to volume ratio), magnetic nanoparticles also have dipole-dipole interaction which tends the particles to aggregate compared to other non-magnetic counterparts. Thus the particles have to be stabilized which can be done in two ways: either by steric stabilization or by electrostatic stabilization. Steric stabilization is attained by attaching long chain surfactants on to the surface of nanoparticles to prevent the particles from approaching closer, thereby overwhelming the attractive components which tend the particles to aggregate. Electrostatic stabilization is achieved by introducing surface charge onto the nanoparticles, which results in electrostatic repulsion of nanoparticles, hence leading to stabilization of the dispersion.

Number of synthetic strategies are available for the synthesis of particles in organic media at elevated temperatures which leads to hydrophobic fairly monodispersed nanoparticles. Palma et al in Chem Mater 2007, 19, 1821-1831 reported synthesis where hydrophobic ligands are exchanged with hydrophilic to make these particles water dispersible, but the synthesis steps include high temperature as well as harmful organic solvents. Another problem with high temperature synthesis is to keep the bio-molecules at the surface of the particles biologically active at the synthesis temperature or on cooling at room temperatures. Other methods include microemulsion, hydrothermal or sonochemical, which are also not effective in producing the particles with requisite properties.

In biomedical applications, another prerequisite of the nanoparticles is large surface area to volume ratio that allows for the increased loading of therapeutics thereby making them useful in drug delivery.

Curcumin (CUR) a yellow polyphenol compound found in the rhizomes of the plant *curcuma longa* is known for its excellent anti-oxidant, anti-cancer, anti-inflammatory, and anti-microbial activities, which makes it a promising candidate for coating on iron oxide nanoparticles for biomedical applications. The coating of curcumin on iron oxide nanoparticles with linkers like oleic acid, chitosan and silica has been reported Tran et at in Colloids Surf. A: Physicochem. Eng. Aspects, 2010, 371, 104-112 has reported the synthesis of $Fe_3O_4$ nanoparticles-curcumin conjugate where curcumin is attached to nanoparticles by using linkers like chitosan and oleic acid. In the above mentioned work, curcumin is indirectly attached onto the magnetite nanoparticles via a linker. Also the author mentions that curcumin is only being adsorbed onto the chitosan or oleic acid coated magnetite nanoparticles. The linker mentioned could not improve the water dispersibility of the prepared fluid.

An article titled "Curcumin-loaded magnetic nanoparticles for breast cancer therapeutics and imaging applications" by Murali M Yallapu, Shadi F Othman et. al. in Int J Nanomedicine. 2012; 7: 1761-1779 having doi: 10.2147/IJN.S29290 disclose formulation composed of an iron oxide core coated with β-cyclodextrin (CD) and pluronic F68 polymer (polyethylene oxide-co-polypropylene oxide-co-polyethylene oxide) and loading anticancer drug curcumin. The article further discloses preparation of magnetic nanoparticles comprising dissolving cyclodextrin, solution of iron(3+) and iron(2+) ions (molar ratio 2:1) in water, ammonium hydroxide, pluronic polymer F68 stirring, washing drying to obtain magnetic nanoparticles (MNC) and followed by loading of curcumin solution in acetone, facilitating the penetration of curcumin molecules (CUR) into the CD or CD-F68 polymer layers in the formulation. MNP-CUR exhibited individual particle grain size of ~9 nm and hydrodynamic average aggregative particle size of ~123 nm.

Article titled "Superparamagnetic iron oxide nanoparticles: magnetic nanoplatforms as drug carriers" by Wahajuddin and Sumit Arora et. al in Int J Nanomedicine. 2012; 7: 3445-3471 having doi: 10.2147/IJN.S30320 relates to superparamagnetic iron oxide nanoparticles (SPIONs) which are small synthetic .gamma.-Fe2O3 (maghemite) or Fe3O4 (magnetite) particles with a core ranging between 10 nm and 100 nm in diameter as novel drug delivery vehicles. The magnetite nanoparticles are obtained by co-precipitation of iron(3+) and iron(2+) ions (molar ratio 2:1) which are further coated with suitable polymers, liposomes, dendrimers etc. Drug loading is achieved either by conjugating the therapeutic molecules on the surface of SPIONs or by coencapsulating drug molecules along with magnetic particles within the coating material envelope.

Article titled "Biomedical properties and preparation of iron oxide-dextran nanostructures by MAPLE technique" by Carmen S Ciobanu, Simona L Iconaru et. al in Chemistry Central Journal 2012, 6:17 doi:10.1186/1752-153X-6-17 relate to dextran coated iron oxide nanoparticles thin films. The dextran-iron oxide continuous thin films are obtained by MAPLE technique from composite targets containing 10 wt. % dextran as well as 1 and 5 wt. % iron oxide nanoparticles synthesized by co-precipitation method. The particle sized calculated was estimated at around 7.7 nm.

Article titled "Encapsulation and Sustained Release of Curcumin using Superparamagnetic Silica Reservoirs" by Suk Fun Chin, K. Swaminathan Iyer et. al having DOI: 10.1002/chem.200802747 disclose synthesis of Fe3O4 nanoparticles by using spinning-disc processing with $Fe^{2+}/Fe^{3+}$ in aqueous $NH_4OH$. The as-synthesized $Fe_3O_4$ nanoparticles were 8-10 nm in size. The article further discloses encapsulation of $Fe_3O_4$ nanoparticles and curcumin in mesoporous silica capsules.

The prior art reports on the synthesis of conjugates of magnetic nanoparticles and curcumin with a linker or binder are observed to neither increase the stability of the resulting magnetic fluid nor do they enhance the property of the magnetic iron oxide core or non-magnetic curcumin shell.

OBJECTS OF THE INVENTION

Main object of the present invention is to provide biocompatible curcumin or its derivatives directly coated on magnetite nanoparticles for biomedical applications.

Another object of the present invention is to provide a simple one-pot process for direct coating of the curcumin onto the surface of the nanoparticle so that the hydrodynamic size can be minimized which is desirable for biomedical applications.

Yet another object of the present invention is to provide a process for the synthesis of biocompatible ultra-small iron oxide nanoparticles at low temperature thereby reducing the possibility for decomposition of the biomolecule used for coating.

SUMMARY OF THE INVENTION

Accordingly, present invention provides a curcumin coated magnetite nanoparticles, which are biocompatible, stable curcumin or its derivatives coated ultra-small super paramagnetic iron oxide nanoparticles devoid of any linker or binder that retains the medicinal, radical scavenging and fluorescence properties of curcumin, for biomedical applications.

In an embodiment of the present invention, curcumin is directly coated on ultra-small super paramagnetic iron oxide nanoparticles.

In one embodiment of the present invention, curcumin coated ultra-small super paramagnetic iron oxide nanoparticles is of 3 nm size.

In an embodiment, present invention provides a simple one-pot process for the synthesis of curcumin coated magnetite nanoparticles, which are biocompatible, stable curcumin or its derivatives coated ultra-small superparamagnetic iron oxide nanoparticles in absence of a linker or binder comprising;

a. dissolving aqueous mixture of $FeCl_3.6H_2O$ and $FeCl_2.4H_2O$ in the molar ratio ranging between 1.5:1 to 2:1 in a base under inert atmosphere and stirring until complete formation and growth of magnetite nanoparticles;

b. adding dilute mineral acid to the solution as obtained in step (a) until pH 9;

c. adding drop wise curcumin solution dissolved in a base to the solution of step (b) under inert atmosphere, maintaining the pH 9 followed by stirring the dispersion at a temperature in the range of 50-100° C. followed by cooling;

d. dialysing the dispersion of step (c) against water to remove excess curcumin and drying in vacuum to obtain the product.

In another embodiment of the present invention, the base used is selected from alkali hydroxide preferably ammonium hydroxide.

In yet another embodiment of the present invention, the mineral acid used is preferably nitric acid.

In yet another embodiment, present invention provides a method for magnetic as well as fluorescent imaging and other biomedical applications comprising providing curcumin coated magnetite nanoparticles, which are biocompatible, stable curcumin or its derivatives coated ultra-small iron oxide nanoparticles devoid of any linker or binder, the curcumin coated magnetite nanoparticles being used as a contrast agent.

In yet another embodiment, present invention provides a method for delivering curcumin to a subject in need thereof comprising administering curcumin coated magnetite nanoparticles, which are biocompatible, stable, curcumin or its derivatives coated ultra-small iron oxide nanoparticles devoid of any linker or binder.

In yet another embodiment, present invention provides use of curcumin coated magnetite nanoparticles, which are biocompatible, stable curcumin or its derivatives coated ultra-small iron oxide nanoparticles devoid of any linker or binder as contrast agent for magnetic as well as fluorescent imaging and other biomedical applications.

In yet another embodiment, present invention provides use of curcumin coated magnetite nanoparticles, which are biocompatible, stable, curcumin or its derivatives coated ultra-small iron oxide nanoparticles devoid of any linker or binder for delivering curcumin to a subject in need thereof.

DETAILED DESCRIPTION OF INVENTION

The term 'magnetite nanoparticles' as used herein mean and refer to super paramagnetic iron oxide nanoparticles.

Abbreviations: $M_0$—uncoated magnetite sample.

M2 or insitu coated sample—insitu coated superparamagnetic iron oxide nanoparticles.

M1 or CuF—curcumin coated ultra-small superparamagnetic iron oxide nanoparticles (Post synthesis functionalised sample).

Curcumin being non-toxic, biocompatible, fluorescent and having novel medicinal properties, can act as a multi-functional probe in coated nanoparticles. The uptake of $Fe_3O_4$-curcumin conjugate can be monitored by both fluorescent as well as magnetic imaging and hence has advantages over other coated nanoparticles in biomedical applications. Further, considering the high affinity of metal ions to the hydroxyl groups of curcumin, the invention provides a simple process for preparing ultra-small superparamagnetic nanoparticles of iron oxide on which curcumin or its derivatives can be coated directly without losing the medicinal properties of curcumin.

In accordance with the above, the present invention disclose biocompatible, stable curcumin or its derivatives coated ultra-small super paramagnetic iron oxide nanoparticles devoid of any linker or binder, that retains its medicinal, radical scavenging and fluorescence properties of curcumin.

The curcumin molecule is directly attached on to the surface of magnetite nanoparticles through its enolic hydroxyl group without losing its medicinal properties.

The invention relates to a simple one-pot process for the preparation of curcumin or its derivatives coated ultra-small superparamagnetic iron oxide nanoparticles in absence of a linker or binder.

The process employed is a co-precipitation technique since the method does not require any harmful precursors and can be carried out at various temperatures to control size, morphology, dispersity etc. The reaction can be tuned by varying pH of the reaction medium, due to the difference in acidity of the phenolic and enolic hydroxyl groups. The process allows for direct coating of curcumin on to the surface of ultra-small magnetite nanoparticles while retaining the medicinal properties of curcumin.

The process includes the following steps:
1. dissolving aqueous mixture of $FeCl_3.6H_2O$ and $FeCl_2.4H_2O$ in the molar ratio 2:1 in a base under inert atmosphere and stirring until complete formation and growth of magnetite nanoparticles;
2. adding dilute mineral acid to the above solution until pH 9;
3. adding drop wise curcumin solution dissolved in a base to solution of step 2, under inert atmosphere, maintaining the pH 9, and stirring the dispersion at a temperature of 50-100° C. followed by cooling;
4. dialysing the dispersion of step 3 against water to remove excess curcumin and drying in vacuum to obtain the desired product.

The process is carried out in inert atmosphere, preferably nitrogen or argon atmosphere, to prevent oxidation of magnetite nanoparticles The base is selected from alkali hydroxides, preferably ammonium hydroxide and the mineral acid is preferably dil. nitric acid.

Curcumin coated ultra-small superparamagnetic iron oxide nanoparticles (USPIONs) obtained is 3 nm in size.

Accordingly, to a mixture of $FeCl_3.6H_2O$ and $FeCl_2.4H_2O$ (as precursors) in water in a molar ratio 2:1 is added a base under argon atmosphere. The mixture is stirred for complete formation and growth of magnetite nanoparticles. pH of the dispersion is brought to pH 9 by addition of dilute nitric acid, curcumin dissolved in base is added dropwise to the dispersion while maintaining the pH 9. The temperature of the solution is slowly raised to a temperature in the range of 50-100° C. and the mixture is stirred under argon atmosphere for about 30 min. The resulting stable dispersion is then cooled to room temperature (21 to 40° C.) and dialysed against water in a cellulose membrane to remove excess curcumin followed by drying in vacuum to obtain the desired product.

Figure 1:
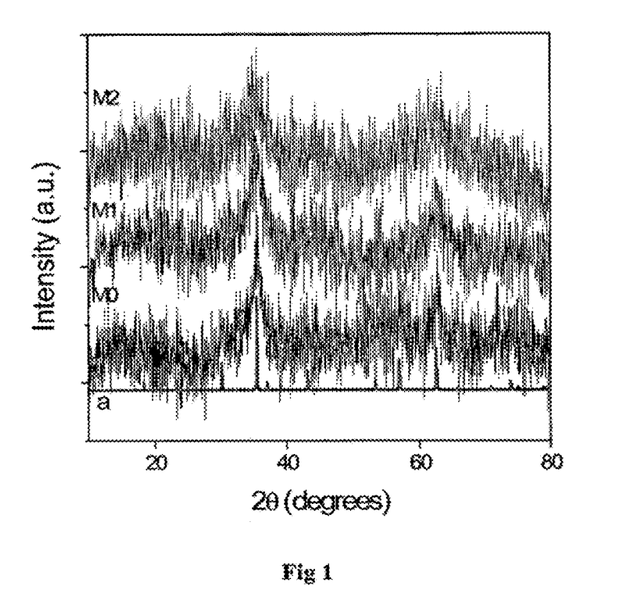
FIG. 1 depicts X-ray diffraction (XRD) patterns of standard Joint Committee on Powder Diffraction Standards (JCPDS) data (19-0629) of $Fe_3O_4$ (a), M0, M1 and M2 samples.

The present invention provides the synthesis of uncoated iron oxide nanoparticles by the co-precipitation process described above for comparison of the XRD pattern of the as synthesized nanoparticles is shown in FIG. 1.

Accordingly, a mixture of $FeCl_3.6H_2O$ and $FeCl_2.4H_2O$ (as iron precursors) in water in the molar ratio 2:1 in a base under nitrogen atmosphere and stirring until complete formation and growth of magnetite nanoparticles followed by adding dilute mineral acid to the above solution until pH 9.

The uncoated and curcumin coated iron oxide nanoparticles are designated as UnF (M0) and CuF (M1) respectively for further studies.

The uncoated and curcumin coated iron oxide nanoparticles are characterized using powder X-ray diffraction (XRD) (FIG. 1). The average crystallite sizes of uncoated and coated samples are in the range of 7 nm and 4 nm respectively. (Particle size decreases for coated particles because coating prevents particle aggregation).

Room temperature magnetic measurements of curcumin coated (CuF) and uncoated (UnF) samples reveal that magnetization of both coated and uncoated samples do not get unsaturated even at a magnetic field of 3 T. Further, no hysteresis loops are observed for both the samples (zero coercivity) indicating both are super paramagnetic. The magnetization at 3 T for uncoated sample is observed to be 30 emu/g and for coated sample is 11 emu/g. The decrease in saturation magnetization compared to the uncoated sample can be ascribed to the reduced size after coating which increases the contribution from the magnetically dead layer from the surface of the particles and the non-magnetic coating layer (curcumin) over each particle. (The non magnetic dead layer is curcumin which reduces the overall mass of iron oxide nanoparticles)

The curcumin coated nanoparticles as well as uncoated particles show no coercivity and remanence, as inferred from M-H measurements at room temperature and therefore, are superparamagnetic.

The coating of curcumin onto the magnetite nanoparticles is further analysed by IR spectroscopy which shows significant change in the position of various peaks in comparison to curcumin as such.

The scavenging property of the as synthesized curcumin coated iron oxide nanoparticles is analysed. The sample is treated with hydrogen peroxide to check whether the radical scavenging property of curcumin is retained. The percentage of $H_2O_2$ scavenging by curcumin and other scavengers is calculated using the formula $H_2O_2$ scavenging effect (%)=(1-$A_s$/$A_c$)×100 where $A_c$ is the absorbance of the control and $A_s$ is the absorbance in the presence of curcumin.

In a particular scavenging activity assay, hydrogen peroxide in phosphate buffer is added to the dispersion of curcumin coated iron oxide nanoparticle (CuF) in phosphate buffer. The mixture is incubated for about 15 min and the absorbance of the solution is measured at 230 nm of $H_2O_2$) using a UV-Visible spectrophotometer.

The $H_2O_2$ scavenging effect of curcumin coated iron oxide nanoparticle (CuF) of the present invention is about 62% as compared to the 81% scavenging activity of 30 ppm curcumin solution confirming the radical scavenging property of curcumin even after coating on SPIONs.

Since the phenolic group is known for the antioxidant activity of curcumin, the study confirms that phenolic hydroxyl group remains free on the curcumin coated on nanoparticles.

That the scavenging activity of curcumin coated nanoparticle is retained is further confirmed by XRD, IR and magnetic measurement of $H_2O_2$ treated and untreated samples as detailed in the example below.

From the measurements described below, it can be concluded that the curcumin coated nanoparticles are highly stable and can be reused for peroxide scavenging as well as for other applications as there is no structural damage observed after peroxide treatment.

Figure 4:
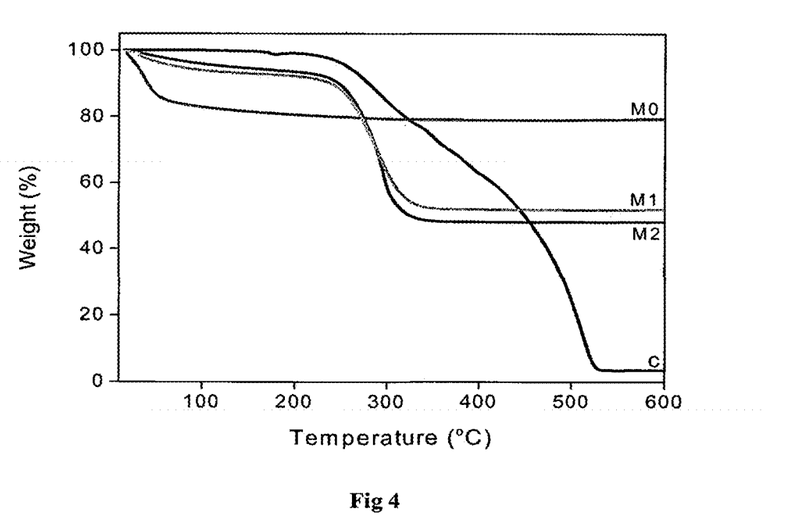
FIG. 4 depicts Thermo gravimetric analysis (TGA) curve for curcumin (C or CUM), M2, M1 and M0 samples.

The thermogravimetric studies of the synthesized samples are carried out between 100-600° C. in air to evaluate the extent of coating of curcumin onto the magnetite nanoparticles. FIG. 4 shows the TGA curve for the samples. TGA gives quantitative as well as qualitative evidences for coating of the nanoparticles. It gives an idea about the bonding strength of the ligand to the nanoparticles, its thermal stability and also it quantifies the coverage of ligand onto the nanoparticles. Accordingly, thermogravimetric analysis reveals that approximately 45% of curcumin is coated on the nanoparticles. Weight loss corresponding to the loss of a small amount of adsorbed water is observed in the case of coated nanoparticles (CuF) when compared to nearly 20% loss for the uncoated particles (UnF).

The biocompatible, stable curcumin coated ultra-small iron oxide nano-particles synthesized by the process of the instant invention exhibited reasonable colloidal stability, magnetization as well as fluorescence properties. Curcumin are effectively coated on to the magnetite nanoparticles, in absence of any linker or binder, and successfully retains its hydrogen peroxide scavenging activity. Moreover, the nanoparticles are stable and comparable with that obtained by using linkers as observed from the relaxivity measurements using NMR technique that give values closer to that reported for well-established magnetic resonance imaging (MRI) contrast enhancement agents like citric acid and dextran coated iron oxide nanoparticles.

The present invention relates to a method for magnetic as well as fluorescent imaging, and other biomedical applications comprising providing biocompatible, stable, curcumin coated ultra-small iron oxide nanoparticles devoid of any linker or binder as a contrast agent.

The present invention relates to a method for delivering curcumin to a subject in need thereof comprising administering biocompatible, stable, curcumin coated ultra-small iron oxide nanoparticles devoid of any linker or binder.

The present invention relates to the use of biocompatible, stable, curcumin coated ultra-small iron oxide nanoparticles devoid of any linker or binder for magnetic as well as fluorescent imaging, and other biomedical applications.

The present invention relates to the use of biocompatible, stable, curcumin coated ultra-small iron oxide nanoparticles devoid of any linker or binder for delivering curcumin to a subject in need thereof.

In sum, the biocompatible, stable curcumin coated ultra-small iron oxide nanoparticles devoid of any linker or binder prepared by the process of instant invention provides curcumin coated is suitable for improved blood residence time, thereby proving to be an efficient candidate for drug delivery and as contrast agent in MRI, apart from the medicinal properties of curcumin. Also, the magnetic property of iron oxide core and fluorescent property of curcumin shell are suitable for use in magnetic as well as fluorescent imaging, indicating the possible multifunctional applications of curcumin coated USPIONs.

The curcumin coated nanoparticles or nanofluids of the invention are such that the terminal OH groups of curcumin or its derivatives are retained thereby retaining its medicinal, radical scavenging and fluorescence properties of curcumin.

In another aspect, the invention provides a simple one-pot process for the synthesis of curcumin or its derivatives coated ultra-small superparamagnetic iron oxide nanoparticles in absence of a linker or binder comprising adding a solution of curcumin in base to a solution of magnetite nanoparticles or nanofluids at low temperature and at pH 9.

The magnetite nanoparticles on which curcumin is coated is prepared using $FeCl_3.6H_2O$ and $FeCl_2.4H_2O$ as iron precursors, wherein $Fe^{2+}$:$Fe^{3+}$ molar ratio is 1:2 and adding the precursors to a base solution, stirring to obtain magnetite nanoparticles and adjusting the pH to 9 with a dilute mineral acid.

In an aspect, the biocompatible, stable curcumin coated ultra-small iron oxide nano-particles synthesized by the process of the instant invention exhibited reasonable colloidal stability, magnetization as well as fluorescence properties. Curcumin are effectively coated on to the magnetite nanoparticles, in absence of any linker or binder, and successfully retains its hydrogen peroxide scavenging activity. Moreover, the nanoparticles are stable and comparable with that obtained by using linkers.

The curcumin coated iron oxide nanoparticles find application as nanofluid in biomedical applications such as contrast enhancement in Mill, magnetic hyperthermia, drug delivery and cancer treatment.

EXAMPLES

The following examples are given by way of illustration therefore should not be construed to limit the scope of the invention.

Example 1

Synthesis of Curcumin Coated Super Paramagnetic Iron Oxide Nanoparticles (M1)

To a mixture of 20 ml of iron precursor solution (0.1M $FeCl_3.6H_2O$ and 0.05M $FeCl_2.4H_2O$) dissolved in water was added 100 ml of 10N ammonium hydroxide under argon atmosphere. The solution was stirred for about 20 minutes for complete formation and growth of magnetite particles. This was followed by addition of dilute nitric acid to bring down the pH to ~9. Curcumin solution (0.5 g curcumin dissolved in ammonium hydroxide, pH~9) was added drop wise to the dispersion. The resultant dispersion was stirred under argon atmosphere for another 30 minutes and the temperature of the solution was raised to 80° C. The resulting stable solution was cooled to room temperature and was dialysed against water in a cellulose membrane for 3 days to remove excess curcumin followed by drying in a vacuum oven at 50° C. to obtain the product.

Example 2

Insitu Coated Super Paramagnetic Iron Oxide Nanoparticles (M2)

0.5 g of curcumin was added to 100 ml 10 N ammonium hydroxide solution and deaerated under argon atmosphere. To this 20 ml iron precursor solution was added and stirred for 20 minutes for complete formation of curcumin coated nanoparticles. The obtained dispersion was dialysed for 3 days to remove excess curcumin and then dried in a vacuum oven at 50° C. The sample was labelled as M2. The preliminary characterisation shows that the phenolic and enolic OH of the curcumin is utilised in binding with nanoparticle. Hence further characterisation was done only for M1 sample, which is further labelled as CuF.

Example 3

Preparation of Uncoated Super Paramagnetic Iron Oxide Nanoparticles (Mo)

To a mixture of 20 ml of iron precursor solution (0.1M $FeCl_3.6H_2O$ and 0.05M $FeCl_2.4H_2O$) dissolved in water was added 100 ml of 10N ammonium hydroxide under argon atmosphere. The solution was stirred for about 20 minutes for complete formation and growth of magnetite particles.

Example 4

Characterization
Powder X-Ray Diffraction Studies

Powder X-ray diffraction patterns were recorded on a PAN alytical X'PERT PRO model X-ray diffractometer, in the 2.theta. range of 10 to 80 degrees.

The uncoated and curcumin coated iron oxide nanoparticles were characterized using powder X-ray diffraction (XRD).

XRD patterns of standard JCPDS data (19-0629) of $Fe_3O_4$ (a), $M_0$ (uncoated sample, UnF), M1 (post synthesis functionalised magnetite nanoparticles, CuF) and M2 (insitu coated nanoparticles)

The crystallographic information of the synthesized nanoparticles was obtained from X-ray diffraction studies. The X-ray diffraction studies revealed that the iron oxide phase formed was biocompatible magnetite and the crystallite size obtained was around 5 nm. Uncoated magnetite nanoparticles were also synthesized by the same procedure for comparison the XRD pattern of the as synthesized nanoparticles is shown in FIG. 1.

The uncoated (M0, UnF) and curcumin coated (M2, CuF) iron oxide nanoparticles were characterized using powder X-ray diffraction (XRD). The XRD patterns of the uncoated (UnF) and curcumin coated (CuF) samples matched well with the standard pattern of magnetite (JCPDS #19-0629). The average crystallite size was calculated using the Scherrer formula, $D=0.91\lambda/\beta \cos\theta$, where $\lambda$ is the wavelength of X-rays (Cu K$\alpha$1.542 A°), $\beta$ is the full width at half maximum (FWHM) after correcting for the instrumental contribution, and $\theta$ is the Bragg angle. The average crystallite sizes of uncoated and coated samples were obtained as 7 nm and 4 nm, respectively.

TEM Image

TEM analysis was performed on a FEI, TECNAI G2 TF30 instrument. Samples were prepared by placing a drop of dilute dispersion on carbon coated 200 mesh copper grid and imaged at an accelerating voltage of 300 kV.

The TEM image of the curcumin coated particles (M2, CuF) show isolated particles (FIG. 2) with average size of ~3 nm which was in close agreement with average crystallite size calculated from XRD. On the other hand, the TEM image of the uncoated sample (M0, UnF) showed highly agglomerated clusters. This indicated that curcumin was efficiently chemisorbed on a nanoparticle and was sterically separating the individual particles in the system.

IR Analysis

IR studies were carried out on a Perkin Elmer Spectrum-One FTIR spectrometer in the frequency range of 400-4000 cm-1 by properly mixing the sample with spectroscopic grade KBr.

Figure 3:
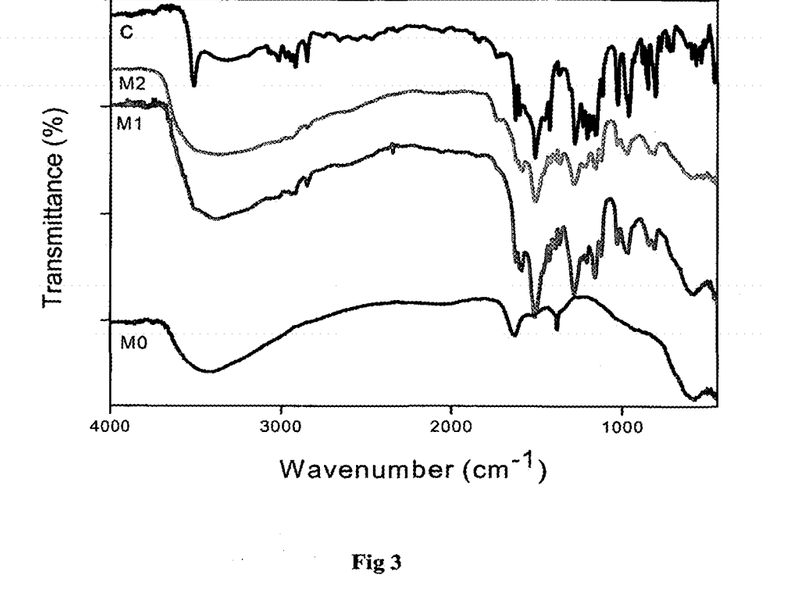
FIG. 3 depicts the Fourier transform infrared spectroscopy (FTIR) spectra of Curcumin (c), M2, M1 and M0 samples.

The presence of curcumin on the surface of the magnetite nanoparticles was qualitatively monitored using IR spectroscopy. The broad band at 590 $cm^{-1}$ was observed due to the Fe—O—Fe stretching vibration of magnetite. A comparison of the spectra of the coated sample and curcumin shows that most of the IR bands of curcumin were present in the spectra of the coated particles. However, curcumin coated iron oxide nanoparticles (M2, CuF) showed significant changes in the position of various bands of curcumin. The intensity of the sharp band at 3510 cm-1, corresponding to 2-phenolic OH and 1-enolic OH was decreased after coating on the nanoparticles. The reduced intensity of the band indicated that some of the OH groups of curcumin are free in the functionalized sample. The pH adopted for the reaction was about 9, at which only the enolic OH will be ionized, whereas at a pH above 9 all the three OH will be ionized. The C=O stretching band at 1628 cm-1 of curcumin was shifted to 1621 cm-1 indicating that a chemical bond was formed between nanoparticle surface and the ligand through the enolic OH. The bands corresponding to C=C stretching and —C—C=O in-plane bending also shifted slightly, whereas there was no considerable shift for the in-plane bending of C—CH and C=CH of the aromatic ring (FIG. 3).

The bands relating to the aromatic ring were not at all affected after coating which suggested that the OH group on the aromatic ring remained intact without taking part in the coating.

Thermogravimetric Analysis

Thermograms of the synthesized samples were recorded on a Perkin Elmer TGA7 analyzer in air.

Thermogravimetric analysis (FIG. 4) of the as-synthesized sample was carried out from room temperature to 600° C. to know the extent of coating. The thermogram shows that approximately 45% curcumin was coated on the nanoparticles. Weight loss corresponding to the loss of a small amount of adsorbed water was observed in the case of coated nanoparticles when compared to nearly 20% loss for the uncoated particles.

Room Temperature Magnetic Measurements Magnetic measurements were done on a Quantum Design MPMS 7T SQUIDVSM. Zero field cooled (ZFC) and field cooled (FC) magnetization measurements were done at 50 Oe and room temperature magnetic measurements were done from −3 T to +3 T.

Figure 5A:
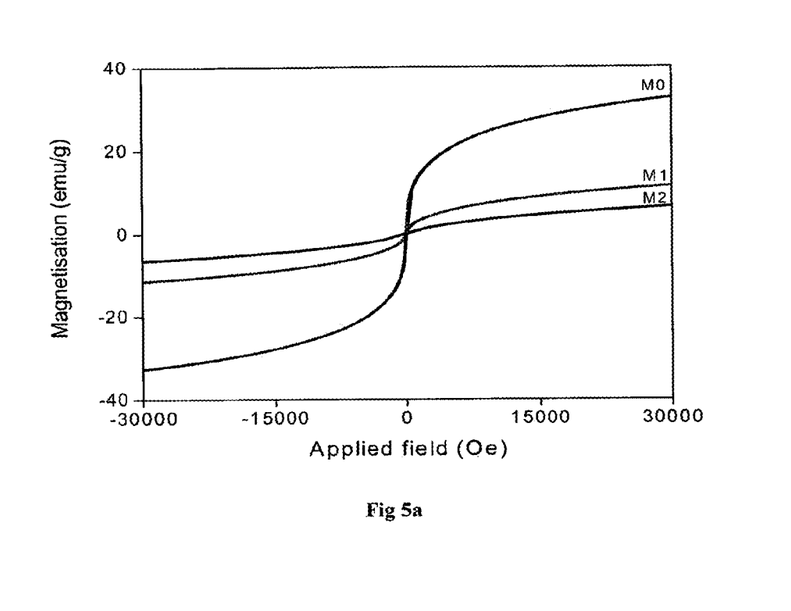
FIG. 5a depicts room temperature Magnetic measurements.

Room temperature magnetic measurements (FIG. 5) of the curcumin coated and uncoated samples show that the magnetization of both uncoated and coated samples did not get saturated even at a magnetic field of 3 T. Also, no hysteresis loops were observed for both samples (zero coercivity), indicating that both samples are super paramagnetic. The magnetization at 3 T for M0 (UnF) was 30 emu/g whereas that of the coated sample (M2, CuF) was 11 emu/g. The decrease in the magnetization of coated nanoparticles compared to that of the uncoated sample can be attributed to the presence of the non-magnetic surface curcumin layer over the nanoparticles as well as the smaller particle size. Further, the effectiveness of coating of curcumin on the nanoparticles was studied by temperature dependent magnetic measurements. The inter-particle magnetic interactions (both dipolar as well as exchange) was suppressed if the coating was effective.

Figure 2:
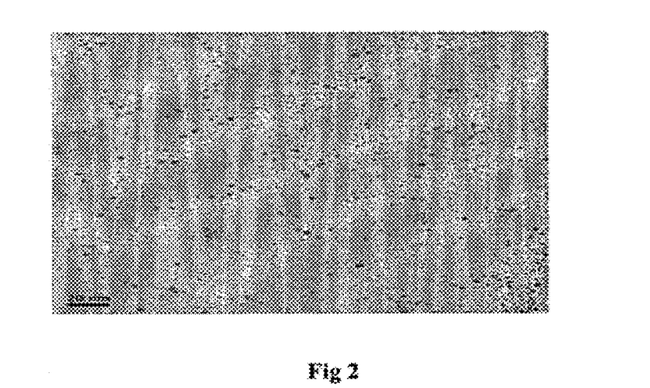
FIG. 2 depicts Transmission electron microscopy (TEM) image of curcumin coated ultra-small super paramagnetic iron oxide nanoparticles.
Figure 5B:
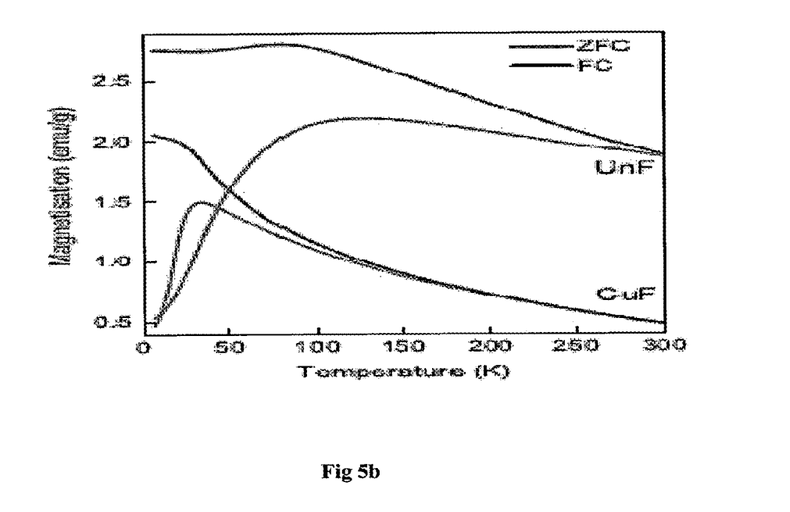
FIG. 5b depicts Zero field cooled (ZFC)/field cooled (FC) curves for uncoated and curcumin coated iron oxide nanoparticles. The measurements were done in a constant small applied field of 50 Oe.

Direct comparison of the nature of the zero field cooled (ZFC) and field cooled (FC) magnetization curves provided information on the inter-particle interactions, and particle size distribution. The ZFC and FC magnetization curves were measured in a field of 50 Oe (FIG. 6). In the ZFC measurement, when the particles are cooled to the lowest temperature, the magnetic moments of individual particles are randomly oriented and the magnetization tends to be zero, and once when a field is applied while heating back to room temperature, the moments tend to align in the direction of the magnetic field up to a specific temperature known as the super paramagnetic blocking temperature. The temperature was proportional to the volume of the particles through the relation, $KV \approx 25 k_B TB$ where V is the volume of a particle and TB is the blocking temperature. K is the total magnetic anisotropy from various contributions, and $k_b$ is the Boltzmann constant. Above this temperature, the thermal energy was sufficient enough to overcome the anisotropic energy and hence the magnetization decreased. Narrow particle size distribution resulted in a narrower peak in the ZFC magnetization curve and a broad peak was expected when the size distribution was wide. The narrow ZFC curve of coated sample, compared to the broad curve for uncoated iron oxide particles, explained mono dispersity of the system, which was clearly reflected in the TEM image. The FC curve remains almost constant below the blocking temperature for the uncoated sample whereas the magnetization decreases continuously after coating. This is an indication for the reduced inter-particle interactions after coating. Similarly, the lower blocking temperature of the coated sample was also an indication for the reduced anisotropy contribution from inter-particle interactions. Thus, the magnetic studies indicate that curcumin was effectively coated on the iron oxide nanoparticles.

Hydrogen Peroxide Scavenging Assay of Curcumin Coated Iron Oxide Nanoparticles 1 ml solution of 40 mM $H_2O_2$ in phosphate buffer (pH=7.1) was added to 4 ml (15 ppm) dispersion of the coated nanoparticles in phosphate buffer (pH=7.1). The mixture was incubated for 15 minutes and the absorbance was measured at 230 nm which is the lmax of hydrogen peroxide. The percentage of $H_2O_2$ scavenging by the sample was calculated using the equation, $$H_2O_2 \text{ scavenging effect (\%)}=(1-A_s/A_c)\times 100$$

where $A_c$ is the absorbance of the control and $A_s$ is the absorbance of the sample.

The scavenging activity of the coated sample was obtained as ~62% compared to the 81% scavenging activity of 30 ppm curcumin solution. This showed that curcumin retained its radical scavenging property even after coating on the SPIONs, confirming that the anti-oxidant activity of curcumin was retained after coating. The phenolic hydroxyl group is known to be responsible for the strong anti-oxidant property of curcumin, and the present study confirms that the phenolic hydroxyl group is remaining free on the curcumin coated on the nanoparticles, supporting the conclusions from other studies. The XRD pattern of the sample after $H_2O_2$ scavenging activity assay was identical to that of the untreated sample, indicating that the hydrogen peroxide did not interact with the magnetite core. Similarly, the IR and UV-Visible spectra of hydrogen peroxide treated and untreated samples were also found to be similar. The hydrogen peroxide scavenging assay was further performed on the treated sample, which gave a scavenging activity closer to that obtained initially. The XRD pattern, IR and UV-visible spectra of the sample again gave a similar result to that of the first one. These results confirmed that the curcumin coated nanoparticles are highly stable and could be reused for peroxide scavenging as well as for other applications, since there was no structural damage observed after the peroxide treatment.

UV-Visible and Fluorescence Spectra of the Curcumin Coated Nanoparticles Dispersed in Ethanol are Compared with that of Pure Curcumin.

Figure 6A:
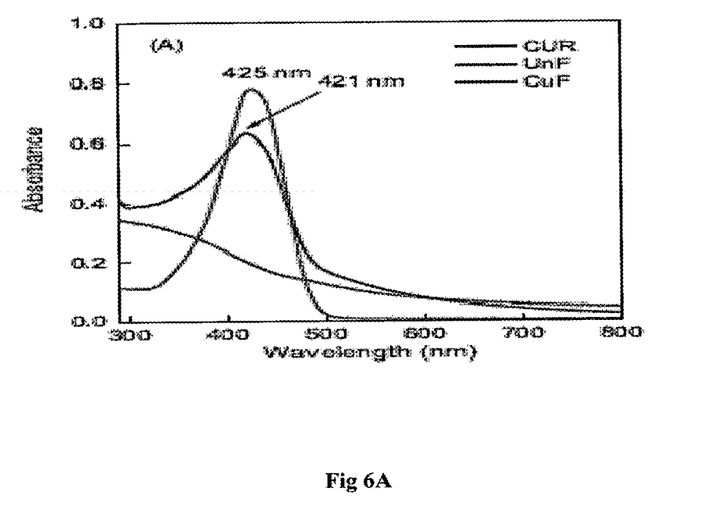
FIG. 6(A) UV-Vis spectra of CuF, UnF and Curcumin (CUR)
Figure 6B:
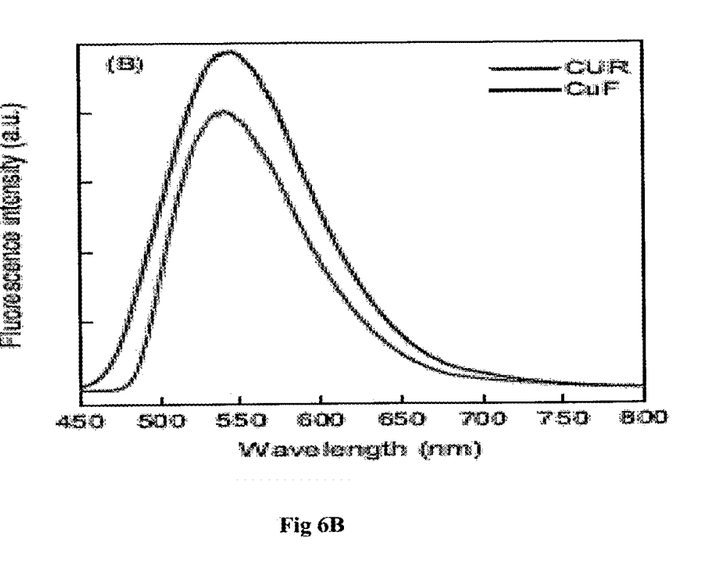
FIG. 6(B) Fluorescence absorption spectra of CuF and CUR measured at an excitation wavelength of 430 nm.

Curcumin shows a peak at 425 nm in UV-visible spectra corresponding to the .pi.-.pi.*transition. The curcumin encapsulated samples shows a bathochromic shift of about 4 nm as shown in (FIG. 6A). The shift in the peak position is attributed to the changes in the environment of curcumin, as evidenced from the IR spectra. The emission property of fluorescent CUR molecule is known to depend on the polarity of its environment. Fluorescence spectra of the coated sample (FIG. 6B) show a small red shift which results from the polar environment around curcumin. This further confirms that the curcumin molecule is coated on the SPIONs Magnetic Resonance Imaging (MIR)

Magnetic resonance imaging demands the use of contrast agents for enhancing the quality of images. The role of the contrast agents is to efficiently vary the relaxivity of water protons. The relaxation of protons occurs by two pathways namely the longitudinal (T1 relaxation) and transverse (T2 relaxation). Depending on these relaxation processes, the contrast agents are classified as T1 and T2 contrast agents. Gadolinium complexes act as T1 contrast agents whereas iron oxide nanoparticle efficiently alters the T2 values of water protons surrounding the particle. The magnetic nanoparticles in a tissue environment when subjected to a magnetic field produce a heterogenous field gradient allowing the water protons to diffuse. The dipolar coupling between the magnetic moments of water protons and that of the particles lead to spin dephasing and T2 relaxation, resulting in reduced signal intensity, and hence termed as negative contrast enhancement.

Figure 7A:
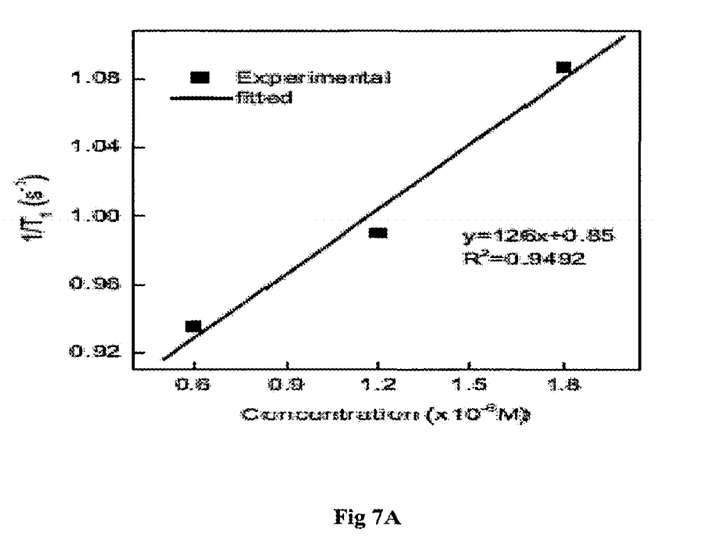
FIGS. 7A and 7B depicts plots to determine R1 and R2 from T1 and T2 measured at different concentrations.
Figure 7B:
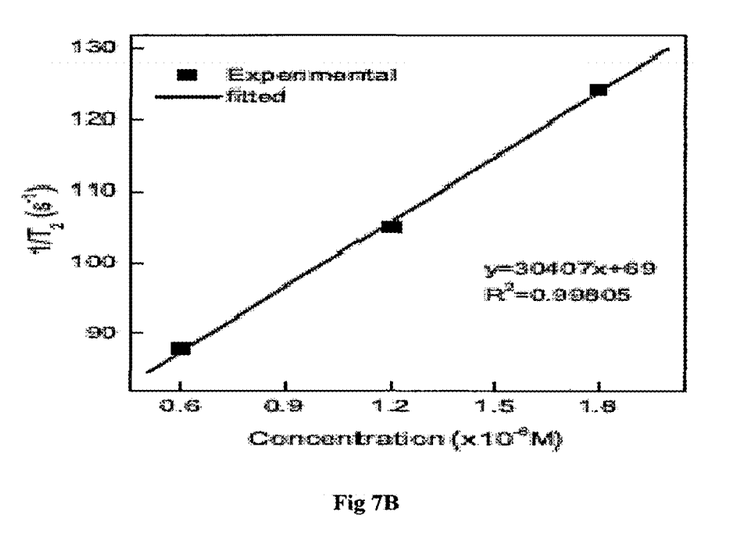
Figure 8:
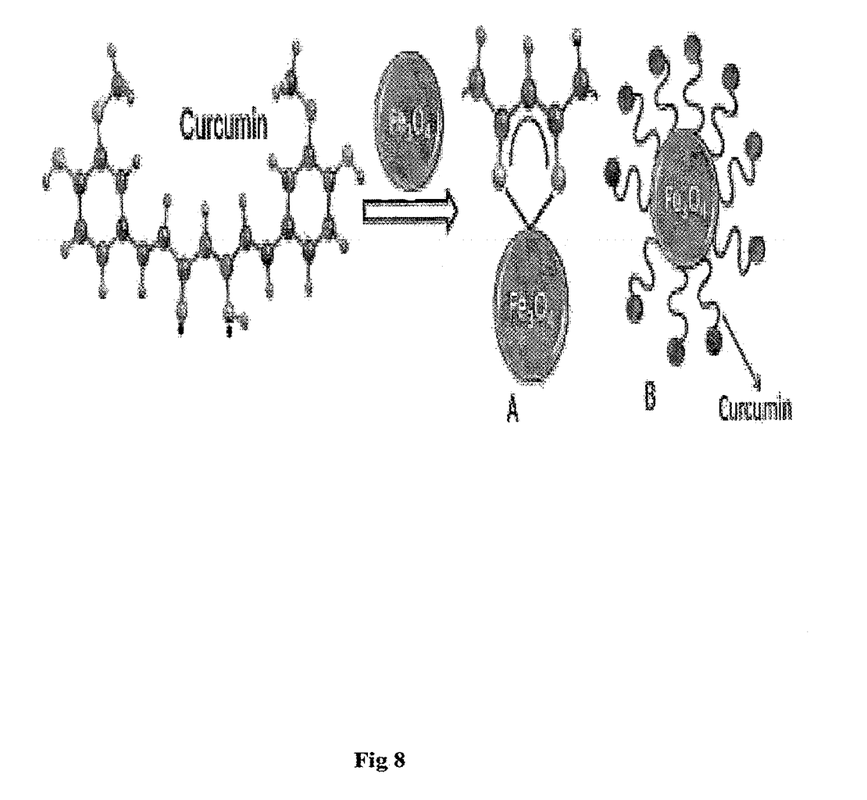
FIG. 8 depicts the photographs of the dispersion of curcumin coated nanoparticles and curcumin in DMSO before and after illuminated with a UV lamp at 365 nm, indicating the fluorescence nature of the coated nanoparticles.

Iron oxide nanoparticles with core diameter less than 10 nm (USPION) produces positive contrast enhancement in T1 weighted images. Iron oxide nanoparticles with effective surface coating was observed to be a promising candidate as contrast agents in MRI as they do not need a targeting probe to image tumors. T1 and T2 measurements were carried out at 400 MHz for three different concentrations of the nanoparticles dispersed in DMSO. The corresponding relaxation rate enhancements of the suspension, R1 and R2, which represent per millimolar concentration of Fe ions present was calculated by determining the number of magnetic Fe ions per particle. The calculation is based on the consideration that each unit cell has eight magnetic ferric ions. The relaxivities of the synthesized SPIONs were calculated from the T1 and T2 values, by accounting for the number of magnetic iron ions present per particle. The normalized values were obtained as 30407 $s^{-1}$ $mM^{-1}$ for transverse relaxivity and 126 $s^{-1}$ $mM^{-1}$ for longitudinal relaxivity (FIG. 7). Since a 3 nm $Fe_3O_4$ contains ~192 Fe3+ ions contributing to the magnetic moment, longitudinal R1 and transverse R2 relaxivities were calculated as 0.66 $s^{-1}$ $mM^{-1}$ and 158 $s^{-1}$ $mM^{-1}$ respectively. The R2/R1 value was calculated as 240 at 400 MHz which was much larger than the minimum threshold value (=2) required for effective negative contrast. This indicates that the curcumin coated USPION is a suitable candidate for use in MRI as a contrast agent. The R2/R1 ratio greatly depends on the applied magnetic field. However, not much variation was observed for citrate coated nanoparticles when measured at the normal MM frequency range of 60 MHz and at 300 MHz which is close to the frequency used for the present measurement (FIG. 7). The ratio gives information on how much nuclear longitudinal magnetization is available after each subsequent acquisition for averaging the signal, and the ratio depends on the magnetic moment of the single particle. The relatively larger value of the relaxivity ratio for the curcumin coated sample indicates that it is a better contrast agent for MM with the additional benefits of the medicinal and fluorescence properties of curcumin.

ADVANTAGES OF THE INVENTION

1. Simple one pot process
2. Biocompatible iron oxide nanoparticles synthesized, as it does not require any harmful precursors
3. It may be used for contrast enhancement in MRI, magnetic hyperthermia, drug delivery, cancer treatment and other related applications
4. It may be used equally for in-vivo as well as in-vitro applications

The invention claimed is:
1. A one-pot process for the synthesis of curcumin coated magnetite nanoparticles, which are biocompatible, stable curcumin coated ultra-small super paramagnetic iron oxide nanoparticles devoid of a linker or binder, the process comprising:
 (a) dissolving aqueous mixture of $FeCl_3.6H_2O$ and $FeCl_2.4H_2O$ in the molar ratio ranging between 1.5:1 to 2:1 in a base under inert atmosphere and stirring until complete formation and growth of magnetite nanoparticles;
 (b) adding dilute mineral acid to the solution as obtained in step (a) until the solution has a pH of about 9;
 (c) adding drop wise curcumin solution dissolved in a base to the solution of step (b) under inert atmosphere, maintaining the pH at about 9 followed by stirring the dispersion at a temperature in the range of 50-100° C. followed by cooling; and
 (d) dialysing the dispersion of step (c) against water to remove excess curcumin and drying in a vacuum to obtain the product.
2. The process according to claim 1, wherein the base used is an alkali hydroxide.
3. The process according to claim 2, wherein the alkali hydroxide is ammonium hydroxide.
4. The process according to claim 1, wherein the mineral acid used is nitric acid.
5. The process according to claim 1, wherein the curcumin coated magnetite nanoparticles have a particle size of about 3 nm.

* * * * *